United States Patent [19]

Yamada et al.

[11] Patent Number: 4,665,205
[45] Date of Patent: May 12, 1987

[54] PROCESS FOR PREPARING TETRAHYDROFURAN

[75] Inventors: Tadashi Yamada; Katsuhisa Yamaguchi, both of Tokuyama, Japan

[73] Assignee: Idemitsu Petrochemical Co., Ltd., Tokyo, Japan

[21] Appl. No.: 801,555

[22] Filed: Nov. 25, 1985

[51] Int. Cl.$^4$ .................................. C07D 307/08
[52] U.S. Cl. ............................................. 549/509
[58] Field of Search ................................ 549/509

[56] References Cited

U.S. PATENT DOCUMENTS 4,093,633  6/1978  Tanabe et al. ................ 549/509
4,197,248  4/1980  Copelin et al. ............... 549/509
4,271,081  6/1981  Murib et al. ............... 549/509 X

FOREIGN PATENT DOCUMENTS 39427    10/1978  Japan.
56-40699  9/1981  Japan.
108029    7/1982  Japan.
108030    7/1982  Japan.

Primary Examiner—Richard L. Raymond
Attorney, Agent, or Firm—Frishauf, Holtz, Goodman & Woodward

[57] ABSTRACT

A process for preparing tetrahydrofuran which comprises steps of;
(i) subjecting 1,4-butanediol to dehydration reaction, and
(ii) subjecting the reaction product obtained from the dehydration reaction in step (i) to extractive distillation, while supplying 1,4-butanediol as the extraction solvent to the system.

14 Claims, 1 Drawing Figure ated at 100° to 200° C. and 1 to 10 Kg/cm², re-
PROCESS FOR PREPARING TETRAHYDROFURAN

BACKGROUND OF THE INVENTION

This invention relates to a process for preparing tetrahydrofuran, particularly to a novel process for preparing tetrahydrofuran in which preparation steps are simplified and which contributes remarkably to energy saving.

Tetrahydrofuran has been widely used in various fields as a solvent for various organic compounds or high polymers and also as an intermediate of various organic compounds. Recently, tetrahydrofuran has further found its use as a starting material or an auxiliary for synthetic polymers such as textiles and plastics, and thus is gaining increasing importance.

As one of processes for preparing tetrahydrofuran, there may be mentioned a process in which 1,4-butanediol (tetramethyleneglycol) is subjected to dehydration reaction in the presence of an acidic catalyst such as sulfuric acid and a cation exchange resin. (See, for example, Japanese Patent Publication No. 40699/1981 and Japanese Unexamined Patent Publication No. 108029/1982 and 108030/1982.)

The resulting reaction product obtained from the above dehydration reaction is a mixture of the desired tetrahydrofuran and water.

Therefore, in order to obtain tetrahydrofuran, it is necessary to isolate tetrahydrofuran from the reaction product. However, tetrahydrofuran and water constitute an azeotropic mixture and thus they cannot be separated from each other by a simple procedure.

From the viewpoint described above, there have been proposed the following methods for separating both components, tetrahydrofuran and water, from each other:

(1) a method in which distillation is effected in the presence of a drying agent such as sodium hydroxide and potassium carbonate; (2) a method in which an azeotropic distillation is effected in the presence of a third substance capable of constituting an azeotropic composition with at least one of both components; (3) a method in which an extractive distillation is effected in the presence of a solvent having an extremely strong affinity to either of both components.

However, in the above methods, a third substance having no direct relationship to the reaction system is employed and thus its procedure becomes complicated and cannot be an advantageous one for an industrial application.

Further, Japanese Patent Publication No. 39427/1978 discloses a method in which water contained in tetrahydrofuran is stripped by an azeotropic distillation under suitable conditions. However, it cannot be an advantageous one in which preparation steps are simplified.

SUMMARY OF THE INVENTION

An object of this invention is to provide a process for preparing tetrahydrofuran in which the conventional problems described above are solved and also preparation steps can be simplified and energy can be saved, by employing 1,4-butanediol which is a starting material as an extraction solvent.

The process for preparing tetrahydrofuran according to this invention comprises steps of;

(i) subjecting 1,4-butanediol to dehydration reaction, and (ii) subjecting a reaction product obtained from the dehydration reaction in the step (i) to extractive distillation, while supplying 1,4-butanediol as an extraction solvent to the system.

DESCRIPTION OF THE PREFERRED EMBODIMENTS

Figure 1:
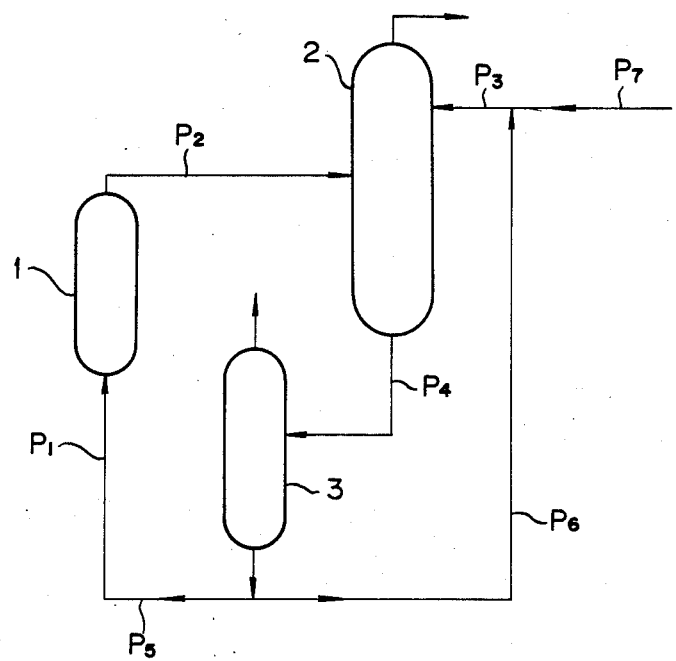
FIG. 1 is a diagram showing one example of processes according to the invention.

This invention will be explained in more detail by referring to a process diagram illustrated in the attached drawing.

First of all, numeral 1 denotes a reaction column in which a catalyst such as sulfuric acid or a cation exchange resin is contained. To the column 1, 1,4-butanediol is introduced through a conduit $P_1$, then dehydration reaction of 1,4-butanediol proceeds therein.

During the reaction, temperature and pressure are controlled at 100° to 200° C. and 1 to 10 Kg/cm², respectively.

From the top of the reaction column 1, is obtained a reaction product comprising a mixture of tetrahydrofuran and water. This reaction product is led to an extractive distillation column 2 through a conduit $P_2$. To this column 2, 1,4-butanediol is further charged as an extraction solvent to effect a continuous extractive distillation. The extractive distillation column 2 may be of a conventional type and is not limited critically.

The thus obtained liquid which is fed to a tray in the concentration part of the extractive distillation column 2 where it is to be extracted, said tray contains 1,4-butanediol extraction solvent in an amount of 40 to 95 mole %, preferably 60 to 80 mole %. In the extractive distillation column 2, temperature and pressure are controlled at 40° to 200° C., preferably 60° to 120° C. and at 0.1 to 10 kg/cm², preferably 0.5 to 4 kg/cm², respectively.

Then, from the top of the extractive distillation column 2, is obtained tetrahydrofuran containing essentially no water and from the bottom of the column is obtained, a mixture of water and the 1,4-butanediol used as an extraction solvent.

If this mixture is introduced to a water-stripping column 3 through a conduit $P_4$ at a temperature of 40° to 230° C. and under a pressure of 0.05 to 1 kg/cm², water-free 1,4-butanediol with high purity can be recovered from the bottom of the column, and from the top of the column, water is discharged from the system.

The recovered 1,4-butanediol is partially transported to the reaction column 1 through a conduit $P_5$, while being kept at heated condition without cooling, while the rest of 1,4-butanediol is transported to the extractive distillation column 2 through a conduit $P_6$ to recycle it. Here, $P_7$ denotes a conduit for supply of 1,4-butanediol.

As is apparent from the above descriptions, this process has many advantages as listed below and thus has a remarkable industrial value:

(1) In this process, preparation steps can be extremely simplified as shown in the process illustrated in FIG. 1, since 1,4-butanediol which is a starting material is employed also as an extraction solvent.

(2) Since, after used as an extraction solvent, 1,4-butanediol can be transported to the column 1 through a column 3, with being kept at a heated condition, it becomes unnecessary to preheat the starting material, thereby contributing to saving energy.

(3) It becomes unnecessary to subject an extraction solvent to recovery treatment which otherwise would be required.

This invention will be described in detail below, by referring to the following Examples, by which this invention should not be limited at all.

EXAMPLE

Example 1

Into a reaction column 1, was placed 1.0 g of 97% aqueous surfuric acid solution and then 1,4-butanediol was charged thereto at a flow rate of 90.0 g/hr, at a temperature at 130° C. and a pressure under 1 kg/cm$^2$. Dehydration reaction of 1,4-butanediol took place to give 90.0 of an aqueous 80% by weight tetrahydrofuran solution (water content: 20% by weight).

Then the resulting solution was introduced to an extractive diltillation column at a flow rate of 90.0 g/hr and after 1,4-butanediol was further introduced therein at a flow rate of 200.0 g/hr, continuous extraction distillation was effected.

From the top of the column maintained at 66° C., tetrahydrofuran with a water content of 0.1% by weight or less was distilled out at a flow rate of 72.0 g/hr, and from the bottom of the column, a mixture comprising 91.8% by weight of 1,4-butanediol and 8.2% by weight of water was discharged.

The extractive diltillation column used was composed of 5 extraction-solvent-recovery sections, ten concentration sections and 30 recovery sections, and operated under atmospheric pressure and at a reflux ratio of 0.5.

Next, the thus obtained mixture was introduced to a column composed of five concentration sections and five recovery sections. From the top of the column was obtained water and from the bottom of the column was obtained 1,4-butanediol with a water content of 0.05 % by weight or less under atmospheric pressure.

Example 2

The apparatus was operated in the same manner as in Example 1 except that the flow rate of 1,4-butanediol was 90.0 g/hr and the reflux ratio was 0.2.

From the top of the extrative distillation column, was distilled tetrahydrofuran with a water content of 0.2% by weight, at a flow rate of 72.1 g/hr, and from the bottom of the column was discharged a mixture comprising 83.4% by weight of 1,4-butanediol and 16.6% by weight of water.

We claim:

1. A process for preparing tetrahydrofuran which comprises the steps of:
   (i) contacting 1,4-butanediol with a dehydration catalyst to dehydrate said 1,4-butanediol thereby forming a reaction mixture containing tetrahydrofuran; and
   (ii) contacting said reaction mixture in an extractive distillation column at a temperature of from 40° to 200° and a pressure of from 0.1 to 10 kg/cm$^2$ with 1,4-butanediol as an extraction solvent and recovering tetrahydrofuran as one stream from said extractive distillation column and 1,4-butanediol as a second stream.

2. The process of claim 1, wherein said 1,4-butanediol is contacted with said dehydration catalyst at a temperature of 100° to 200° C. and a pressure of 1 to 10 kg/cm$^2$.

3. The process of claim 1, wherein said second stream containing 1,4-butanediol also contains water and said water is stripped from said butanediol which is then recycled to contact said dehydration catalyst.

4. The process of claim 3, wherein water is stripped from said 1,4-butanediol at a temperature of 40° to 230° C. and a pressure of 0.05 to 1 kg/cm$^2$.

5. The process of claim 4, wherein said 1,4-butanediol is contacted with said dehydration catalyst at a temperature of 100° to 200° C. and a pressure of 1 to 10 kg/cm$^2$.

6. The process of claim 1, wherein said dehydration catalyst is sulfuric acid.

7. The process of claim 2, wherein said dehydration catalyst is sulfuric acid.

8. The process of claim 3, wherein said dehydration catalyst is sulfuric acid.

9. The process of claim 4, wherein said dehydration catalyst is sulfuric acid.

10. The process of claim 5, wherein said dehydration catalyst is sulfuric acid.

11. The process of claim 1, wherein said dehydration catalyst is a cation exchange resin.

12. The process of claim 2, wherein said dehydration catalyst is a cation exchange resin.

13. The process of claim 4, wherein said dehydration catalyst is a cation exchange resin.

14. The process of claim 5, wherein said dehydration catalyst is a cation exchange resin.

* * * * *